United States Patent [19]

Hunger

[11] Patent Number: 4,923,452

[45] Date of Patent: May 8, 1990

[54] APPARATUS FOR TENDING A STOMA

[75] Inventor: Gerd Hunger, Munich, Fed. Rep. of Germany

[73] Assignee: E. R. Squibb & Sons, Inc., Princeton, N.J.

[21] Appl. No.: 112,233

[22] Filed: Oct. 20, 1987

Related U.S. Application Data

[63] Continuation-in-part of Ser. No. 863,106, May 15, 1986, abandoned, and a continuation of Ser. No. 494,039, May 12, 1983, abandoned.

[30] Foreign Application Priority Data

May 13, 1986 [DE] Fed. Rep. of Germany ....... 3218092

[51] Int. Cl.⁵ ............................................... A61F 5/44
[52] U.S. Cl. .................................................. 604/338
[58] Field of Search .......................... 604/277, 332–345

[56] References Cited

U.S. PATENT DOCUMENTS

| | | | |
|---|---|---|---|
| 3,123,074 | 3/1964 | Turner | 604/332 |
| 3,331,370 | 7/1967 | Notley, Sr. | 604/342 |
| 4,213,458 | 7/1980 | Nolan et al. | 604/344 |
| 4,419,100 | 12/1983 | Alexander | 604/339 |

OTHER PUBLICATIONS

Condensed Chemical Dictionary, Tenth Edition, Van Nostrand Reinhold Co., N.Y., N.Y., 'Silicone', 1981, p. 921.

Primary Examiner—Jerome L. Kruter
Attorney, Agent, or Firm—Scully, Scott, Murphy & Presser

[57] ABSTRACT

The subject matter of the invention is an apparatus for tending a stoma comprising a base plate made of a hypoallergic material or of an adhesive film and a snap ring to which a bag for taking up the excreta is attached with a snap closure. The connection between the base plate and the snap ring is a flexible cylindrical connector piece of little height and a diameter which compared with the base plate is as large as possible. The three-dimensional connector piece extends normal to the base plate and may have also the form of a steep truncated cone.

18 Claims, 2 Drawing Sheets

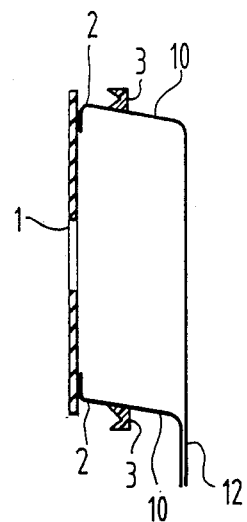
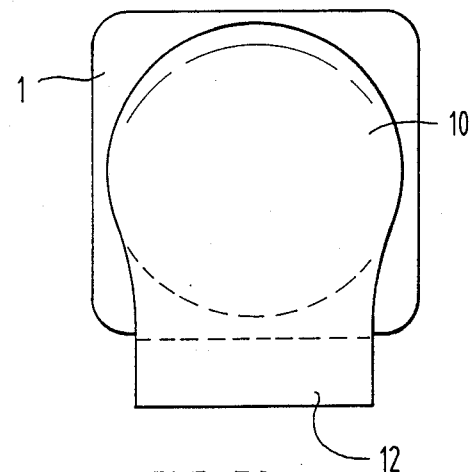
FIG. 3a   FIG. 3b
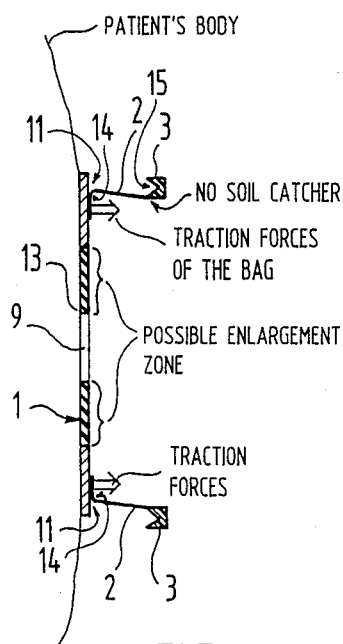
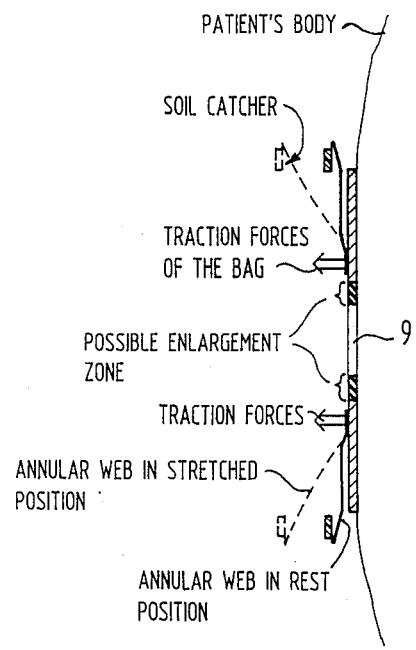
FIG. 4a   FIG. 4b

APPARATUS FOR TENDING A STOMA

CROSS-REFERENCE TO RELATED APPLICATIONS

This in a continuation-in-part of application Ser. No. 863,106, filed May 15, 1986, now abandoned which is a continuation of application Ser. No. 494,039, filed May 12, 1983, now abandoned.

BACKGROUND OF THE INVENTION

The tending of a stoma—i.e. of an artificial outlet for stool (ileostoma, colostoma) or urine (urostoma)—is effected nowadays mainly by means of disposable adhesive bags.

Apart from the (rare) allergy to the adhesive, the adhesive bags involve the disadvantage that when being replaced they tear off or "strip" the uppermost epithelium layers of the skin until it wets and becomes extremely susceptible to irritations and infections. Skin problems around the stomata render the application of adhesive bags impossible in many cases, above all when the stripped skin is additionally exposed to fermentatively aggressive excreta (ileostomy, urostomy) or infectious material (fistulae).

To protect the skin in the immediate vicinity of the stoma, there have been developed base plates of a hypoallergic material, comprising a thin elastic film on the outside of the base plate. The base plates may remain in the applied position for several days. Onto this artificial skin the bags are adhered and are also to be replaced there once or several times a day.

This solution is extremely convenient to the patient (all is flat and flexible) and theoretically represents actually the ideal solution. In practical use, however, there result serious disadvantages. During sitting and stooping, folds are forming in the base plate so that, when the bag is being replaced, an odor and liquid-tight closure is made impossible. Moreover, the covering film of the base plate, which is very thin so as to have as far as possible the elasticity of the skin, is often damaged upon stripping off a bag. The base plate thereby becomes unserviceable and must prematurely be replaced.

To overcome these said disadvantages, it has therefore been suggested to glue directly onto the base plate the semi-rigid ring of a snap closure whose likewise semirigid counterpart is provided at the bag. The closure engages according to the snap-fastener principle and can be replaced. This system solves very well the replacement of the bags but involves other, very inconvenient disadvantages:

1. The closure becomes practically rigid by the junction of the two semi-rigid rings. This rigid closure is very uncomfortable during sitting and stooping—quite particularly when large-size stomata, requiring large-size closures, are involved. The closure exerts a painful pressure on the skin, it detaches, due to its rigidity, the base plate from the elastic skin and finally "uses up" the base plate so that it has to be replaced more often than would be necessary with a fully elastic closure.
2. On account of the inconveniencies during wearing, the patient cannot be expected to put up with a ring larger than absolutely necessary. There is thus required a considerable number of ring sizes both for the base plate and for the bag (at present 5 sizes are commercially available). Production and distribution are thereby rendered more expensive.
3. The tending (care) of the most critical place, namely the skin ring between the circumference of the stoma and the inner edge of the circular opening of the base plate —e.g. by means of a coating paste—is complicated if narrow snap rings are involved. Wide rings allow a good tendance of that critical skin ring but ar bulky and very uncomfortable due to their rigidity.
4. Moreover, excreta are regularly gathering in the circular niche between base plate and snap ring. They can be removed only with difficulty, decompose quickly and lead to additional undesirable odors. They render a clean replacement difficult or impossible.
5. When the bag is being replaced, the new bag must be connected to the ring on the side of the body by pressure. Since said ring is firmly attached to the base plate, it is not possible to exert a counterpressure with the fingers. The pressure necessary for effecting the connection therefore fully acts on the at first mostly very sensitive abdomen of the patient.

The original and correct concept of a flexible connection between base plate and bag has, on account of the difficulties in the bag replacement, been sacrificed thus in favor of a rigid connection, which admittedly enables a simple replacement but involves said disadvantages.

With the particular object to overcome the disadvantages stated above under 1. and 5., there has already been proposed a device (Product Information "Two-Piece Ostomy System", Hollister Inc., March 1982 and U.S. Pat. No. 4,419,100 issued Dec. 6, 1983 to Alexander), in which the ring of the snap closure is not glued to the base plate but connected thereto through a connecting piece, which allows limited floating between the ring and the base plate. The connecting piece is extremely thin or flat resilient, annular web, connected at its outer circumference to the external portion of the back of the snap ring. The connection to the base plate is provided in the central area of the disk around the central opening.

The connection between base plate and snap ring is in this known device still relatively rigid. In the rest position, the snap ring substantially lies directly against the base plate—an all round, even small space between base plate and ring is not provided in that arrangement.

Consequently, the pressure discomfort to the user during stooping and sitting remains substantially unchanged. Since the annular web is fastened to the base plate at its central portion around the central opening, the possibility for the user to enlarge the opening so as to adjust it to his individual requirements is very restricted. In this device, too, various sizes are thus necessary, which renders the production, distribution and use more complicated and expensive.

Moreover, from the fact that the annular web is fastened to the base plate at its central portion and that for the desired "floating" of the ring a considerable distance must exist between the inner adhesion point and the outer circumference of the web to which the ring is attached, it follows that a larger and thus more uncomfortable ring is required for a given stoma size compared with the previous art as described above. Also, the annular web needs to be made of a resilient material because a movement perpendicular to the base plate (resulting when the fingers are inserted between base plate and web) would not be possible with this construction, when using flexible but unresilient material.

Finally, the snap ring of that device comprises on its inner side the necessary undercut for holding the counterpiece, which represents an undesired soil-catcher. Soil is collecting furthermore between the inner region of the bottom side of the ring and the connecting piece.

As advantage of the device known from U.S. Pat. No. 4,419,100 there remains thus substantially only the fact that it is possible to tilt the ring so as to enable to put the fingers below the snap ring and to exert a counterpressure when pressing on the ring provided at the bag. However, due to the close fitting of the snap ring at the base plate, a pressure on the area surrounding the stoma cannot be completely avoided in that device either. In addition any movement with this extremely thin or flat device is only possible by stretching the resilient web, what creates traction forces irritating just the critical peristomal area and tending to separate there the base plate from the skin. As regards the movability of the parts relative to each other, the desired reduction of the number of sizes of the product and the demands concerning the requirements for cleaning, much is still left, however, to be desired.

SUMMARY OF THE INVENTION

It is the main object of the present invention to provide an ostomy device comprising a base plate, a snap ring means for detachably connecting a bag and a connector means connecting said base plate and said ring means, which device guarantees free mobility of the ring means in three dimensions without creating traction forces on the peristomal area thus providing high comfort to the patient.

It is a further object of the present invention to provide an ostomy device as mentioned above which allows the distribution of the pulling or pushing forces created by the full bag or during exchange of the bag away from the small peristomal area to the large peripheral area where the skin is healthy.

It is a further object of the present invention to provide an ostomy device as mentioned above which permits an optimal tending of the immediate circumference of the stoma.

It is a further object of the present invention to provide an ostomy device as mentioned above which is free from soil catchers and therefore can be easily kept clean.

It is still a further object of the present invention to provide an ostomy device as mentioned above which comprises only a relatively small ring means relative to the size of the stoma which is favorable for the comfort of the patient.

It is still another object of the present invention to provide an ostomy device as mentioned above in which the opening in the base plate can be enlarged to a considerable degree and much wider than in the design according to U.S. Pat. No. 4,419,100 in accordance with the individual needs of the patients.

These objects of the invention are achieved by an ostomy device for detachably securing a bag to a stoma comprising:

(a) an apertured base plate, said base plate defining first and second circumferences, said first circumference being smaller than the second with a diameter that may be enlarged to a diameter of the stoma to be tended and a second larger circumference the diameter of which is about 4 to about 20 mm smaller than the edge of the base plate for transmitting traction forces to the skin of the user at a maximum distance from said stoma, (b) a snap ring means substantially parallel to the base plate, the dimension of the aperture of the ring being determined by the diameter of the said second circumference said ring means detachably connecting with a snap closure a bag that receives the excreta from said stoma, and (c) a connector means made of a flexible but nonresilient plastic film material having a thickness of about 0.05 to about 0.3 mm connecting said base plate and said snap ring means, said connector means being cylindrical or having the form of a steep truncated cone and extending substantially perpendicular to said base plate, said connector means being attached to said base plate along said second circumference whereby forces transmitted to said base plate by attachment of said bag to said ring or by the movements of the user to said bag are absorbed by said base plate at said larger circumference to dissipate said forces at a maximum distance from said stoma.

BRIEF DESCRIPTION OF THE DRAWINGS

FIG. 3 shows an embodiment of the invention in which the cylindrical or conical connector piece is likewise extended beyond the snap ring and terminates in a nonreturn valve. FIG. 3a: section parallel to the axis of the cylindrical or conical connector piece; FIG. 3b: topview in the direction of the base plate (snap ring not shown).

FIG. 4 shows the constructive advantages of the device of the invention as compared with the device known from U.S. Pat. No. 4,419,100. FIG. 4a: illustrates the device of the present invention: the opening in the base plate can be enlarged to a considerable extent. Traction forces, e.g. of the filled bag, are directed to an area remote from the stoma. No additional, construction created traction forces. FIG. 4b: illustrates the device of U.S. Pat. No. 4,419,100: the possibility of enlarging the opening of the base plate is very restricted. Moving the ring in the direction perpendicular to the base plate, e.g. when changing the bag, is possible only if the material of the annular web is resilient and can be stretched because the ring is stiff. Also these additional construction related fraction forces are concentrated on the most sensitive area around the stoma—as are the traction forces of the full bag.

DETAILED DESCRIPTION OF THE INVENTION

Figure 1:
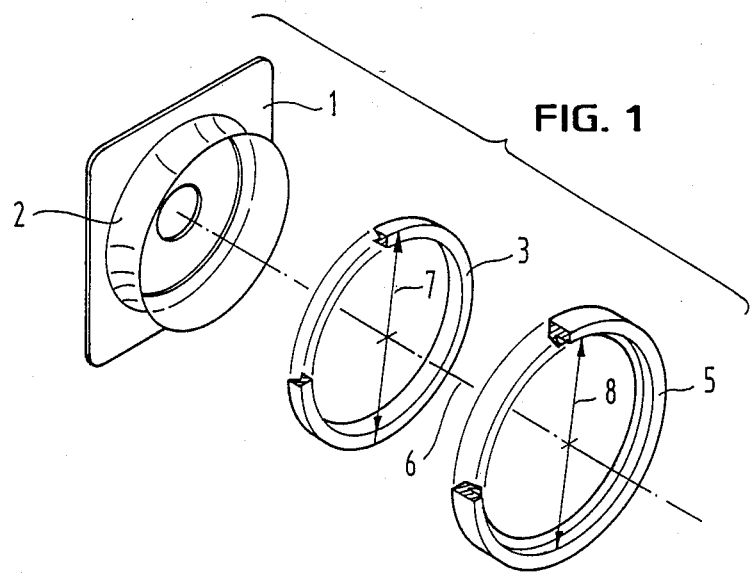
FIG. 1 shows an embodiment of the invention consisting of base plate, flexible cylindrical or conical connector piece welded or glued onto it and snap ring for detachably connecting the bag. The counterpart thereto is the likewise shown snap closure of the bag which comprises a somewhat larger diameter than the snap ring connected to the base plate so that it fits over the latter. (For reasons of clearness, the parts are shown in exploded view in FIG. 1)

In accordance with the present invention the interposition of extremely flat annular resilient web between faceplate and ring according to U.S. Pat. No. 4,419,100 is improved by interposition of a three-dimensional cylindrical, flexible but non-resilient connector piece. This cylinder extends essentially normal to the base plate. It has a diameter as large as possible with a given base plate. Within a reasonable range the snap ring can move freely without any construction-related forces in all three dimensions so allowing change of bags and bending and moving of the wearer whereby its construction guarantees the freedom of traction forces.

This is a decisive advantage compared with the extremely thin or flat annular resilient web of the prior art, where every movement of said ring leads to construction-related traction forces to the peristomal area.

The base plate (1) which preferably has a square form can be made of any one of the materials which are conventionally used for this purpose. It defines a first and a second circumference whereby said first circumference (13) constituting the opening (9) for the stoma is smaller than the second circumference (14) where the connector piece is fixed. The opening (9), may be enlarged to a diameter which corresponds to the diameter of the stoma to be tended. The second, larger circumference (14) is defined by the circle at which the connector piece (2) is attached to the base plate (1). The diameter of said second circumference is as large as possible in relation to the given size of the base plate, being only about 4 to about 20 mm smaller than the edge of the (square) base plate.

The connector piece (2) between base plate (1) and the snap ring (3), which constitutes an essential element of the invention, can be cylindrical or have the form of a steep truncated cone. It consists of a flexible, but substantially non resilient plastic film material which has a thickness of about 0.05 to about 0.3 mm. The term "flexible" designates a material that can be bent easily and repeatedly but which is not elongated by traction forces. A material which is elongated by traction forces and restores its original length, when the force is released, is herein called "resilient". The connector piece (2) has a diameter which compared with the base plate (1) is as large as possible inter alia to ensure an optimum distribution of the traction force of the filled bag. Thereby the danger of a separation of the base plate from the skin is largely excluded, which would happen if the tension is concentrated on a small area. The cylindrical or slightly conical connector piece (2) has a height of at least 1 mm. A height of 3 to 15 mm is preferred.

The connection of the flexible connector piece (2) to the base plate (1) is effected on an annular surface of the base plate which constitutes said second circumference (14) and which has a diameter only insignificantly smaller than that of the snap ring. Accordingly, the connector piece (2) has a cylindrical form or that of a steep truncated cone. Thus, an optimum utilization of the size of snap ring (3) and base plate (1) is achieved since the user can, depending on his individual requirements, widely enlarge the central opening (9) of the base plate(1) and is not confined in this connection by a central adhesion area between base plate and connector piece.

Apart from a cylindrical embodiment of the connector piece, however, also a design of a steep truncated cone is possible and subject matter of the invention. That design is advantageous as regards the discharge from the stoma into the bag but comparatively disadvantageous for other reasons, above all when the cone comprises a greater taper in the direction of the base plate.

Figure 2:
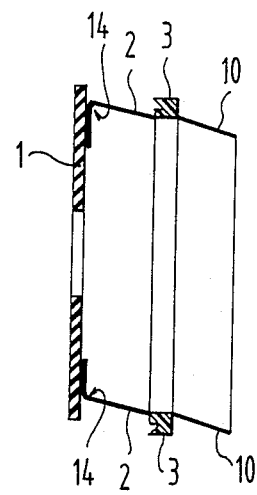
FIG. 2 illustrates a preferred embodiment according to the invention. The circular edge between base plate and cylindrical or conical connecting piece is rounded off. The connecting piece engages at the inner circumference of the snap ring. Thereby the formation of soil-catching edges and niches is prevented. The cylindrical or conical connecting piece is extended beyond the snap ring—optionally by changing its geometric shape—and thus acts as a soil repeller. The undercut is situated on the outside of the snap ring.

The axis (6) of the flexible cylindrical or conical connector piece (2) can be perpendicular to the base plate, or it may be advantageous to direct it obliquely downwards so that the formation of folds is minimal and excreta can flow off spontaneously. For the same reason it is preferred that the edge (11) between base plate (1) and connector piece (2) is rounded off; see FIG. 2.

In the device of the invention a snap ring (3) for detachably connecting a bag is provided at the flexible connector piece (2) before the base plate (1), to which ring the conventional bags with snap closure (5) can be attached and replaced without difficulty. The snap ring (3) for detachably connecting the bag is preferably disposed parallel to the plane of the base plate (1) and is—connected by the connector piece (2)—spaced only some mm therefrom.

The dimension of the aperture of the snap ring is determined by the diameter of the said second circumference (14) at the base plate (1). Any normal bag having a snap closure can be fastened to the snap ring (3) and removed therefrom for replacement.

In the device of the invention the conventional base plates can be used, which consist preferably of a hypoallergic material having a thin elastic film on the outside. However, there may also be used as "base plates" simple films with the adhesives customary in connection with adhesive bags. Since the base plate has to be replaced only at intervals of several days, the skin damaging by stripping is minimal also in this simple and economic embodiment, in contrast to adhesive bags which have to be replaced once or several times a day.

The manner of connecting the connector piece (2) to the base plate (1) is not critical; due to the easy performance, a welding or gluing is preferred in practice. The edge (11) between the base plate (1) and the connector piece (2) is preferably rounded off so as to keep a soiling by excreta as low as possible. For the same purpose the undercut of the body-facing snap ring (15) is provided preferably at the outer circumference of the ring.

The invention comprises the following advantages:

1. The flexible connector piece reduces the discomfort to the patient by the rigid closure, especially if it is sufficiently long and thus provides sufficient clearance.
2. The device preserves the base plate, because the snap closure is spaced apart from the base plate. It can be worn for a longer period (economic advantage) and has to be replaced less frequently (convenience for the patient).
3. The connector piece eliminates soil-catching niches if it seals the inner side of the snap ring facing the base plate. This applies particularly if the inner diameter (8) of the snap bag fits over the outer diameter (7) of the snap ring.
4. Since the connector piece is connected to the base plate in the outer area thereof so as to be more or less coincident with the snap ring, the user of the device according to the invention can enlarge the opening for the stoma in the base plate within relatively wide limits, in accordance with his individual needs. In particular with respect to the large stomata the tending of which is most difficult, there is achieved thereby a more advantageous ratio between the size of the stoma and that of the ring than would be possible with a connection between base plate and connector piece situated in the central area of the base plate as it is the case in U.S. Pat. No. 4,419,100.

5. The connection between the snap ring and the snap closure of the bag can be effected without any traction force on the skin surrounding the stoma which is quite sensitive. In this respect, too, a quite considerable advance is achieved in comparison with the known arrangements.

According to a further improvement, the device of the invention is provided with a soil repeller (10). For this purpose the connector piece (2) is wholly or partially extended beyond the snap ring (3) (see FIG. 3a), with the possibility of being narrowed e.g. to a truncated cone. The snap ring then will not be soiled when the bag is being replaced. A further improvement in this respect is provided by the feature that the film on the base plate as well as the inner side of the movable connector piece is siliconized so as to achieve a complete discharge into the bag. The soil repeller can also be extended to a nonreturn valve (12); see FIG. 3b. Than the sensitive skin in the direct surroundings of the stoma is protected primarily at night against a flowing back of the aggressive or infectious excreta.

What is claimed is:

1. An ostomy device for detachably securing a bag to a stoma comprising:
    (a) an apertured base plate, said base plate defining first and second circumferences, said first circumference being smaller than the second with a diameter enlargeable to a diameter of the stoma to be tended and a second larger circumference the diameter of which is about 4 to about 20 mm smaller than the edge of the base plate for transmitting traction forces to the skin of the user at a maximum distance from said stoma,
    (b) A snap ring means substantially parallel to the base plate, the dimension of the aperture of the snap ring means being determined by the diameter of the said second circumference, said snap ring means adapted to be detachably connected with a snap closure on a bag that receives the excreta from said stoma, and
    (c) a connector means made of a flexible but non resilient plastic film material having a thickness of about 0.05 to about 0.03 mm connecting said base plate and said snap ring means, said connector means being cylindrical or having the form of a steep truncated cone and extending substantially perpendicular to said base plate, said connector means being attached to said base plate along said second circumference whereby forces transmitted to said base plate upon attachment of a bag to said snap ring means or by the movements of the user or by said bag are absorbed by said base plate at said larger circumference to dissipate said forces at a maximum distance from said stoma.

2. A device as claimed in claim 1 wherein said flexible connector means is cylindrical.

3. A device as claimed in claim 1 wherein said flexible connector means has the form of a steep truncated cone.

4. A device as claimed in claim 1 wherein the inner surface of the flexible connector means is coated with silicone.

5. A device as claimed in claim 1 or 2 or 3 wherein said flexible connector is at least 1 mm in length.

6. A device as claimed in claim 1 or 2 or 3 or 4 wherein said flexible connector is at least 3-15 mm in length.

7. A device as claimed in claim 1 or 2 or 3 or 4 wherein said flexible connector has a diameter, which compared to the base plate, is as large as possible.

8. A device as claimed in claim 1 or 2 or 3 or 4 wherein the central axis of the connector means extends downwardly at an angle with respect to a plane defined by the base plate.

9. A device as claimed in claim 1 or 2 or 3 or 4 wherein the connection between the base plate and said flexible connector is formed by rounding off the end of the connector means to define an annular flange which is secured to the base plate.

10. A device as claimed in claim 9 wherein said annular flange is secured to said base plate by welding.

11. A device as claimed in claim 9 wherein said annular flange is secured to said base plate by an adhesive.

12. A device as claimed in claim 1 or 2 or 3 or 4 wherein said snap ring is secured to said connector means along its entire inner circumference.

13. A device as claimed in claim 1 or 2 or 3 or 4 wherein said connector means extends through said ring to define a soil repeller beyond the ring.

14. A device as claimed in claim 13 wherein said soil repeller comprises a non-return valve means.

15. A device as claimed in claim 1 or 2 or 3 or 4 wherein the base plate is secured to the skin by an adhesive.

16. A device for tending a stoma, said device comprising:
    (a) a flexible and elastic base plate means, said base plate being formed from a hypoallergic material and secured to the skin surrounding a stoma with an adhesive layer;
    (b) a snap ring means for detachably connecting a bag that retains excreta from the stoma;
    (c) a flexible connector means connecting said base plate and said snap ring, said flexible means being secured to said snap ring means along the entire innercircumference of said ring.

17. A device for tending a stoma as claimed in claim 16 wherein said connector means extends through said snap ring means to define a soil repeller beyond said ring means.

18. A device for tending a stoma as claimed in claim 17 wherein said soil repeller further includes a non-return valve means.

* * * * *

UNITED STATES PATENT AND TRADEMARK OFFICE
CERTIFICATE OF CORRECTION

PATENT NO. : 4,923,452
DATED : May 8, 1990
INVENTOR(S) : Gerd Hunger

It is certified that error appears in the above-identified patent and that said Letters Patent is hereby corrected as shown below:

On the Title page, Section [30]: "May 13, 1986" should read as --May 13, 1982--

Column 7, line 52, Claim 1: "0.03 mm" should read as --0.3 mm--

Signed and Sealed this

Twelfth Day of November, 1991

Attest:

HARRY F. MANBECK, JR.

Attesting Officer

Commissioner of Patents and Trademarks